United States Patent [19]

Schmitt et al.

[11] Patent Number: 4,647,705

[45] Date of Patent: Mar. 3, 1987

[54] PROCESS FOR IMPROVING THE ULTRAVIOLET LIGHT TRANSMITTANCE OF ETHYLENE GLYCOL

[75] Inventors: Thomas M. Schmitt, Dearborn Heights; George M. Allen, Southgate; Pauls Davis, Gibraltar, all of Mich.

[73] Assignee: BASF Corporation, Wyandotte, Mich.

[21] Appl. No.: 765,683

[22] Filed: Aug. 15, 1985

[51] Int. Cl.$^4$ .................. C07C 29/88; C07C 31/20
[52] U.S. Cl. ..................................... 568/868; 568/871
[58] Field of Search .................. 568/868, 871, 914

[56] References Cited

U.S. PATENT DOCUMENTS

| | | | |
|---|---|---|---|
| 2,768,214 | 10/1956 | McKinley et al. | 568/868 |
| 3,970,711 | 7/1976 | Reiche et al. | 568/868 |
| 4,118,582 | 10/1978 | Walker | 568/871 |
| 4,154,970 | 5/1979 | Beer et al. | 568/868 |
| 4,213,000 | 7/1980 | Coates | 568/868 |
| 4,349,417 | 9/1982 | Rebstat et al. | 568/868 |

FOREIGN PATENT DOCUMENTS

| | | | |
|---|---|---|---|
| 2831210 | 1/1980 | Fed. Rep. of Germany | 568/868 |
| 981965 | 2/1965 | United Kingdom | 568/914 |

*Primary Examiner*—J. E. Evans
*Attorney, Agent, or Firm*—D. Barbara McKenzie-Wardell; Joseph D. Michaels

[57] ABSTRACT

This invention relates to a process for improving the ultraviolet light transmittance of ethylene glycol by treating industrial grade ethylene glycol with an aluminum-nickel alloy in the presence of an alkali compound.

4 Claims, No Drawings

PROCESS FOR IMPROVING THE ULTRAVIOLET LIGHT TRANSMITTANCE OF ETHYLENE GLYCOL

BACKGROUND OF THE INVENTION

1. Field of the Invention

This invention relates to a process for improving the ultraviolet light transmittance of ethylene glycol by treating industrial grade ethylene glycol with an aluminum-nickel alloy.

2. Description of the Prior Art

There are many methods known for producing ethylene glycol. A commonly used method involves the hydration of ethylene oxide at increased temperatures under pressure. The resulting ethylene glycol produced by this method and other methods known in the art contains many impurities and can be designated as industrial grade ethylene glycol. It may be used in antifreeze or other products where highest purity is not required.

The so-called industrial grade ethylene glycol must be distinguished from fiber grade ethylene glycol which is used to make polyesters and other synthetic fibers. Among other requirements, fiber grade must not contain significant amounts of impurities which will result in the low transmittance of ultraviolet light. In order to be acceptable as fiber grade ethylene glycol, the ethylene glycol generally must have an ultraviolet transmittance of at least 70 percent at 220 nanometers, at least 90 percent at 275 nanometers, and at least 95 percent at 350 nanometers.

SUMMARY OF THE INVENTION

The subject invention relates to a process for improving the ultraviolet transmittance of ethylene glycol which comprises treating industrial grade ethylene glycol with an aluminum-nickel alloy. An ultraviolet light transmittance of at least 70 percent at 220 nanometers, at least 90 percent at 275 nanometers, and at least 95 percent at 350 nanometers can be achieved by this process. The resulting ethylene glycol can be used as or for the preparation of fiber grade ethylene glycol.

DESCRIPTION OF THE PREFERRED EMBODIMENTS

For purposes of this discussion industrial grade ethylene glycol will be defined as any ethylene glycol product (it may contain some diethylene glycol, triethylene glycol, ethanol, and the like in addition to other impurities) having an ultraviolet transmittance of less than 70 percent at 220 nanometers, less than 90 percent at 275 nanometers, and less than 95 percent at 350 nanometers.

The methods for preparing industrial grade ethylene glycol are well known in the art, and are particularly disclosed in Kirk-Othmer, *Encyclopedia of Chemical Technology*, v. 11, pp. 933-956 (1980). The choice of method is not that important, but will effect the amount and type of impurities which must be removed from the industrial grade ethylene glycol.

The industrial grade ethylene glycol is treated with an aluminum-nickel alloy and an alkali compound by adding them to the industrial grade ethylene glycol. The object is to expose all of the industrial grade ethylene glycol to the surface of the aluminum-nickel alloy in a basic environment. In view of this objective, it is preferred to agitate the mixture of industrial grade ethylene glycol and aluminum-nickel alloy. It may also be useful to carry out the treatment at increased temperatures and pressures. Any procedure which provides maximum exposure of the industrial grade ethylene glycol to the catalyst surface is desirable.

Primary or unactivated aluminum-nickel alloys are used in the subject process. These alloys are well known in the art and are precursors used for the preparation of Raney nickel catalysts.

The weight ratio of aluminum to nickel is from about 4:1 to about 1:2. The alloys are usually prepared by melting the aluminum and heating to increased temperatures such as 1200° C. The nickel is then added, preferably in the form of small cubes. The nickel then dissolves and an exothermic reaction occurs. After cooling, the alloy is broken by hammering and then pulverized.

The treatment process takes place in the presence of the pulverized aluminum-nickel alloy and an alkali compound such as sodium hydroxide, potassium hydroxide, calcium hydroxide, sodium carbonate, and the like, preferably in stoichiometric amounts based upon the aluminum. The alkali compound is added as an aqueous alkali solution. Generally a 5 percent to 40 percent aqueous alkali solution is sufficient. Sufficient alloy and alkali are added to the industrial grade ethylene glycol to meet the desired transmittance requirements. The amount will depend upon the concentration of the adsorbing impurities.

The following example will serve to illustrate a specific embodiment of the invention. Temperatures are in degrees Celsius and parts are parts by weight unless otherwise specified. Naturally, this disclosure and example are not intended to cover all embodiments of the claimed invention. Many equivalents will be obvious to those skilled in the art.

EXAMPLE

A hydrogenation apparatus was prepared consisting of a hydrogenation vessel, an addition funnel connected to the vessel for adding an alkali solution, and a mercury reservoir connected to the hydrogenation vessel by tubing.

To the hydrogenation vessel were added industrial grade ethylene glycol and an aluminum-nickel alloy such that the weight ratio of ethylene glycol to aluminum-nickel alloy was 75:1. The hydrogenation apparatus was then evacuated to 60 mm Hg. Then a 10 percent solution of NaOH was added in two steps over a 60 minutes period from the addition funnel such that the weight ratio of industrial grade ethylene glycol to NaOH was approximately 15:1.

After the addition of the NaOH, the mixture was allowed to stir for approximately three days. The resulting suspension was decanted, filtered, and distilled. Then the ultraviolet transmission was measured and found to be:

(a) 81 percent at 220 nm
(b) 97 percent at 275 nm
(c) 100 percent at 350 nm.

The corresponding values before treatment were:

(a) 40 percent at 220 nm
(b) 73 percent at 275 nm
(c) 96 percent at 350 nm.

Thus, the treated industrial grade ethylene glycol met the ultraviolet adsorption specification for fiber grade ethylene glycol.

Due to the pyrophoric nature of the spent aluminum-nickel alloy, it should be kept under water and disposed of by dissolving it in 1M hydrochloric acid.

The embodiments of the invention in which an exclusive privilege or property is claimed are defined as follows:

1. A process for improving the ultraviolet transmittance of industrial grade ethylene glycol which comprises treating the industrial grade ethylene glycol with effective amounts of an aluminum-nickel alloy and alkali compound.

2. The process of claim 1 wherein the aluminum-nickel alloy has a weight ratio of aluminum to nickel of from 4:1 to 1:2.

3. The process of claim 2 wherein the aluminum-nickel alloy and alkali compound are used in stoichiometric amounts based upon the aluminum.

4. The process of claim 3 wherein the alkali compound is dissolved in water to form a 5 to 40 percent by weight aqueous alkali solution.

* * * * *